(12) United States Patent
Kay et al.

(10) Patent No.: US 7,642,392 B2
(45) Date of Patent: Jan. 5, 2010

(54) PROCESS FOR PREPARING BRANCHED CHAIN HYDROCARBONS

(75) Inventors: Richard Daniel Kay, Brough (GB); George Ernest Morris, Cottingham (GB); John Glenn Sunley, Cottingham (GB)

(73) Assignee: BP Oil International Limited, Middlesex (GB)

( * ) Notice: Subject to any disclaimer, the term of this patent is extended or adjusted under 35 U.S.C. 154(b) by 224 days.

(21) Appl. No.: 10/569,441

(22) PCT Filed: Aug. 19, 2004

(86) PCT No.: PCT/GB2004/003578

§ 371 (c)(1),
(2), (4) Date: Feb. 24, 2006

(87) PCT Pub. No.: WO2005/023733

PCT Pub. Date: Mar. 17, 2005

(65) Prior Publication Data

US 2007/0004955 A1    Jan. 4, 2007

(30) Foreign Application Priority Data

Sep. 3, 2003   (GB) ................................ 0320684.4

(51) Int. Cl.
*C07C 1/00* (2006.01)

(52) U.S. Cl. ................................................ 585/642
(58) Field of Classification Search ................ 558/179; 560/155, 174; 585/747, 642

See application file for complete search history.

(56) References Cited

U.S. PATENT DOCUMENTS 3,576,898 A     4/1971   Blake et al.
4,543,347 A  *  9/1985   Heyward et al. .............. 502/61

FOREIGN PATENT DOCUMENTS

JP          2108646 A        4/1990
WO    WO 02/070440 A1        9/2002
WO    WO 03/020668 A1        3/2003

OTHER PUBLICATIONS

UK Patent Office Search Report under Section 17, Application No. GB0320684.4, dated May 19, 2004.
Kim et al.; *J. Org. Chem.*; vol. 43, No. 17; pp. 3432-3433 (1978).

* cited by examiner

*Primary Examiner*—Taylor Victor Oh
(74) *Attorney, Agent, or Firm*—Nixon & Vanderhye

(57) ABSTRACT

The present invention relates to a process for the production of branched chain hydrocarbons from methanol and/or dimethyl ether, which process comprises contacting, in a reactor, methanol and/or dimethyl ether with a catalyst comprising indium halide.

18 Claims, No Drawings

PROCESS FOR PREPARING BRANCHED CHAIN HYDROCARBONS

This application is the U.S. National Phase of International Application PCT/GB20041003578, filed 19 Aug. 2004, which designated the U.S. PCT/GB20041003578 claims priority to British Application No. 0320684.4 filed 3 Sep. 2003. The entire content of these applications are incorporated herein by reference.

This invention relates to a process for preparing branched chain hydrocarbons, in particular to a process for preparing a branched chain hydrocarbon product comprising triptane.

Branched chain hydrocarbons may be synthesised by a number of routes. In particular, mixtures of branched chain hydrocarbons may be formed by homologation of methanol and/or dimethyl ether in the presence of a zinc halide catalyst, as described, for example, in GB 1,547,955, U.S. Pat. Nos. 2,492,984, 3,969,427, 4,059,646, 4,059,647, 4,249,031 and WO02/70440.

U.S. Pat. No. 4,249,031, for example, describes a process for the preparation of a hydrocarbon mixture by contacting one or more oxygen-containing organic compounds, such as methanol, with one or more zinc halides.

U.S. Pat. No. 4,059,647, for example, describes a process for the production of triptane (2,2,3-trimethylbutane) comprising contacting methanol, dimethyl ether or mixtures thereof with zinc iodide.

Triptane is a branched chain hydrocarbon of high octane number, which can be used in unleaded aviation gasoline and unleaded motor gasoline (see, for example, WO 98/22556 and WO 99/49003).

We have now found an alternative and/or improved process to produce branched chain hydrocarbons from methanol and/or dimethyl ether.

According to a first aspect, the present invention provides a process for the production of branched chain hydrocarbons from methanol and/or dimethyl ether, which process comprises contacting, in a reactor, methanol and/or dimethyl ether with a catalyst comprising indium halide.

In the present invention the reaction of methanol and/or dimethyl ether produces reaction products comprising branched chain hydrocarbons Preferably, the indium halide is one or more of InX and/or $InX_3$, wherein X is a halide selected from Cl, Br and I, and combinations thereof. More preferably the indium halide is $InX_3$, and most preferably is $InI_3$, although other indium compounds may be present in the reactor.

The indium halide may be introduced to reactor in the form of a compound comprising both indium and at least one halogen atom. Preferably, the indium halide is introduced to the reactor as InX and/or $InX_3$, preferably, $InX_3$, wherein X is a halide selected from Cl, Br and I, and combinations thereof. Most preferably the indium halide is introduced to the reactor as $InI_3$. The indium halide may be introduced to the reactor in the form of an anhydrous salt or may be added in the form of a solid hydrate.

Alternatively, or additionally, the indium halide may be formed in-situ in the reactor, for example, by reaction of a suitable indium source with a halide source in the reactor. Suitable indium sources include, for example, indium compounds such as oxides, hydroxides, acetates, alkoxides, nitrates and sulphates. Suitable halide sources include hydrogen halides and alkyl halides, for example, methyl halides.

As well as the indium halide, the reactor may also contain zinc halide, such as zinc iodide. Preferably, however, no zinc compounds are present in the reactor.

In addition to methanol and/or dimethyl ether reactants, there may also be introduced to the reactor additional feedstock components. Suitable additional feedstock components include hydrocarbons, halogenated hydrocarbons and oxygenated hydrocarbons, especially olefins, dienes, alcohols and ethers. The additional feedstock components may be straight chain, branched chain or cyclic compounds (including heterocyclic compounds and aromatic compounds). In general, any additional feedstock component in the reactor may be incorporated in the products of the reaction.

Certain additional feedstock components may advantageously act as initiators and/or promoters for the reaction to produce branched chain hydrocarbons.

Thus, in one preferred embodiment, the reactor also contains one or more compounds that can act as initiators for the reaction to produce branched chain hydrocarbons. Suitable initiators are preferably one or more compounds (having at least 2 carbon atoms) selected from alcohols, ethers, olefins and dienes.

Preferred initiator compounds are olefins, alcohols and ethers, preferably having 2 to 8 carbon atoms. Especially preferred initiator compounds are 2-methyl-2-butene, ethanol and MTBE.

In a further preferred embodiment, there is also present in the reactor one or more promoters selected from one or more of hydrogen halides and alkyl halides of 1 to 8 carbon atoms. Methyl halides and/or hydrogen halides are preferred. Preferably the halide of the promoter is the same element as the halide of the indium halide catalyst.

Additional feedstock components, including compounds that may act as initiators and/or promoters, may be introduced as "fresh" compounds or mixtures of compounds to the reactor, but may also be formed in-situ in the reactor during the reaction to produce branched chain hydrocarbons. For example, olefins and dienes that may be formed in the reaction may act as initiators. As a further example, alkyl halides, such as methyl iodide, that may be formed may act as promoters. Thus, in one preferred embodiment, either alternatively to or in addition to any "fresh" additional feedstock components introduced to the reactor, additional feedstock components, and especially initiators and/or promoters, may be introduced in to the reactor as components of a suitable recycle stream. Suitable recycle streams may be obtained, for example, by recycle of a portion of a product stream from the reactor, preferably by recycle of at least a portion of a by-product stream formed after separation of desired branched chain hydrocarbons, such as triptane, and any other useful products from said reactor product stream.

As with additional feedstock components in general, any initiators and/or promoters introduced to the reactor may be incorporated in the reaction products.

Water is formed during the reaction of methanol and/or dimethyl ether to produce branched chain hydrocarbons. Optionally, additional water may also be introduced to the reactor.

It has been found that catalysts comprising indium halide can produce branched chain hydrocarbons from methanol. The process may be either a gas or liquid phase process. However, advantageously, the process is operated substantially in the liquid phase.

Accordingly, in a second aspect, the present invention provides a process for the production of branched chain hydrocarbons from methanol and/or dimethyl ether, which process comprises contacting, in a liquid phase reaction composition in a reactor, methanol and/or dimethyl ether with a catalyst comprising indium halide.

In a preferred embodiment of the second aspect of the present invention the liquid reaction composition also comprises at least one additional feedstock component, and most preferably comprises at least one initiator and/or at least one promoter, wherein said additional feedstock components, initiators and promoters are as defined herein.

The process of the second aspect of the present invention allows branched chain hydrocarbons to be formed in a liquid phase reaction at relatively low temperatures, such as 100° C. to 300° C.

In a third aspect, the present invention also provides a continuous or semi-continuous process for the production of branched chain hydrocarbons from methanol and/or dimethyl ether, which process comprises contacting, in a liquid phase reaction composition in a reactor, methanol and/or dimethyl ether with a catalyst comprising indium halide, and at a temperature of at least 100° C., to produce a product mixture comprising (i) methanol and/or dimethyl ether and (ii) a hydrocarbon reaction product comprising branched chain hydrocarbons, and in which process the catalyst is maintained in the reactor in an active form and in an effective concentration.

The catalyst comprising indium halide may be maintained in an active form and in an effective concentration in the reactor by recycling to the reactor, one or more promoter compounds as defined previously, such as, for example, hydrogen iodide and/or methyl iodide from downstream product recovery stage(s).

In a preferred embodiment of the third aspect of the present invention the liquid reaction composition also comprises at least one further additional feedstock component, and more preferably comprises at least one initiator, wherein said additional feedstock components and initiators are as defined herein. Said further additional feedstock component has preferably been recycled from downstream product recovery stage(s)

Preferably, the processes of the present invention are performed substantially in the liquid phase to produce a product mixture comprising methanol and/or dimethyl ether in a first liquid phase and the hydrocarbon reaction product comprising branched chain hydrocarbons in a second liquid phase. However, it may be necessary to cool the product mixture to form the first and second liquid phases. The hydrocarbon reaction product is then usually separated from the mixture.

The first liquid phase is typically a hydrophilic phase comprising at least one of water, methanol and dimethyl ether. The first liquid phase may also comprise the catalyst comprising indium halide. The catalyst may be completely dissolved or there may also be a solid phase present and the catalyst may be partially dissolved in the first liquid phase. The first liquid phase and any solid phase may be retained in the reactor. Alternatively, it may be removed and processed to recover water prior to recycle. Alternatively or additionally, the catalyst may be recovered from the first phase, and optionally, regenerated for re-use.

Precipitation of a solid phase comprising undissolved catalyst components during reaction can cause problems with the operation of a continuous process. In general, it is preferred to remove such precipitated solids, for example, by filtration. Precipitation of solids is a particular problem with the use of zinc halides, such as zinc iodide, as catalysts. It has been found that the formation of such precipitates is avoided or at least significantly reduced using indium halide catalysts of the present invention.

The second liquid phase, if present, is typically a hydrophobic phase comprising the branched chain hydrocarbon product. Other, by-product, hydrocarbon compounds may also be present in the second phase. Examples of possible by-product hydrocarbon compounds include non-branched paraffinic and olefinic hydrocarbons, and aromatic hydrocarbons. The hydrophobic phase is generally less dense than the hydrophilic phase. The hydrophobic phase may also comprise, dissolved therein, one or more of methanol, dimethyl ether, methyl halide (e.g. iodide) and water.

Preferably, a mixture of methanol and dimethyl ether is used in the present invention. This has an advantage that the reaction of dimethyl ether and methanol produces less water than is produced from reaction of methanol alone. If methanol is used in downstream stages of the overall process for the production of branched chain hydrocarbons, for example in scrubbing gaseous effluent or aiding separations, then there may be a limit to the amount of methanol which can be substituted by dimethyl ether in the process if methanol and/or dimethyl ether are recycled from the downstream processes to the reactor.

The processes for production of branched chain hydrocarbons according to the present invention have also been found to have a more advantageous product distribution than for analogous zinc halide reactions. In particular, it has been found that significant amounts of triptane may be formed, and that relative to the amount of triptane formed, less "heavy" products (typically those above $C_8$) and correspondingly more "lighter" products (such as $C_4$ to $C_6$ compounds) are formed during reaction with an indium halide catalyst compared to reaction using a zinc halide catalyst.

Thus, the branched chain hydrocarbon reaction product preferably comprises at least 10% by weight, for example, 10-60% by weight, preferably, 20-50% of triptane by weight.

In the processes of the present invention the methanol and/or dimethyl ether is usually contacted with the indium halide catalyst at a temperature of at least 100° C. Preferably, the methanol and/or dimethyl ether is contacted with the indium halide at a temperature of 100 to 300° C., preferably 100-250° C., more preferably 150 to 250° C. The reaction time of the processes of the present invention is usually 0.1-6 hrs, for example, 0.3-3 hrs. Lower temperatures tend to require longer reaction times. Reaction times or temperatures are usually lower for dimethyl ether than methanol. The times may be the reaction times in a semi-continuous reaction, or residence time (including average residence time) for continuous processes. The reaction of the processes of the present invention may be monitored for conversion of the methanol or dimethyl ether by periodic sampling in the reaction (for a semi-continuous or continuous process) or in reaction effluent for a continuous process, and then analysis by an appropriate technique e.g. gas liquid chromatography or mass-spectroscopy.

The reaction of the processes of the present invention may be performed at ambient pressure, but is usually performed at elevated pressure such as 1-100 barg, preferably 5-100 barg, such as 50-100 barg. The pressure may be autogeneous, or may by provided also by the presence of an added inert gas, such as nitrogen or argon, and/or preferably by the presence of added hydrogen, as further described below.

The ratio of methanol and/or dimethyl ether and water to each other and to the indium halide catalyst employed in the reaction may vary widely. Since methanol, dimethyl ether and water may be present in one or more liquid phases in the reactor and the vapour phase, and the indium halide may be present in liquid or solid phase it is convenient to express the concentrations of methanol, dimethyl ether, water and catalyst components as relative weight parts in the reactor excluding any hydrocarbon components or phase. For example, for a total (excluding hydrocarbon components or phase) of 100 weight parts of methanol, dimethyl ether, water and catalyst, the catalyst is preferably greater than 50 parts and less than 99 parts, more preferably greater than 70 parts and less than 95 parts and most preferably greater than 80 parts and less than 90 parts. The water is preferably less than 50 parts and greater than 0, more preferably less than 25 parts and most preferably less than 10 parts. The balance of methanol and dimethyl ether will be to make 100 weight parts. The hydrocarbon components/phase will be additional to this. The ratio of methanol to dimethyl ether may vary from being all dimethyl ether through to all methanol. If preferred, the composition may be chosen to maximise the solubility of the catalyst in the liquid phase or phases at the reaction temperature but operation of the invention is not limited to reactor compositions where no solid phase is present.

Preferably, the process is performed in the substantial absence of added water, especially with methanol as reactant. As water is a by-product of the process, it may be removed from the reactor as the reaction proceeds suitably to maintain a steady state concentration in the process.

It may also be possible to remove water from the reactor using techniques such as for example, with desiccants, such as magnesium silicate or molecular sieves e.g. zeolites such as 3A or 13X usually in a non acidic form, e.g. in a metal form when the metal may be an alkali metal, for example, Na or K.

It may be useful to recycle some of the separated water product as a wash stream to wash out any catalyst dissolved in the second liquid phase.

The reaction of the present invention may be performed in the presence of hydrogen. Hydrogen may be introduced into the reactor as fresh feed and/or as a component in a recycle stream. Thus, hydrogen may be introduced to the reactor as a separate feed stream, or together with the catalyst and/or one of the other reactants. Alternatively or additionally, the reaction may also be performed in the presence of a hydrogenation catalyst, which may be soluble or insoluble. The catalyst usually comprises a Group VIII metal (CAS notation, as defined in the Periodic Table of the Elements in Advanced Inorganic Chemistry, $5^{th}$ Edition, by Cotton and Wilkinson), for example, Ni, Rh, Pd, Os, Ir, Pt, and Ru. Preferred examples include catalysts consisting essentially of, or comprising ruthenium, nickel and/or palladium. Preferably, a Ru catalyst is employed, optionally, in the presence of Re. The Group VIII metal is, preferably, on an inert support, such as active carbon, for example, charcoal, or alumina, silica or silica/alumina. Amounts of the Group VIII metal in the supported catalyst may be 0.01-30% by weight (expressed as metal): for example, a supported Ni catalyst may comprise 0.01-10% or 10-30% wt Ni.

Preferred catalysts include Ru, Ni or Pd on carbon, Ru on alumina and Ru and Re (in relative wt amounts of 2-6:1) on C. A most preferred catalyst is Ru/C, for example, where the amount of Ru in the catalyst is 0.01-10 wt %.

The reaction of the present invention may be performed in the presence of carbon monoxide. Carbon monoxide may be introduced into the reactor as fresh feed and/or as a component in a recycle stream. Thus, carbon monoxide may be introduced to the reactor as a separate feed stream, or together with the catalyst and/or one of the other reactants. Where both hydrogen and carbon monoxide are introduced to the reactor it is especially desirable to use synthesis gas as a source of both. The presence of carbon monoxide in the reactor will lead to production of branched chain esters, as described, for example, in U.S. Pat. No. 4,166,189, the contents of which are herein incorporated by reference. For the production of branched chain esters, the carbon monoxide, is preferably present in the reactor at a molar ratio of carbon monoxide to methanol of at least 0.25:1, more preferably at least 10:1.

The production of branched chain esters by inclusion of carbon monoxide in the reactor may be further enhanced by inclusion of one or more initiators and/or one or more promoters, as described above, especially by introduction to the reactor of one or more olefins.

In contrast to the above, where it is desired to introduce hydrogen to the reactor but to avoid or reduce the production of branched chain esters it is desirable to use hydrogen containing feed streams with only low carbon monoxide content, such as streams with a molar ratio of hydrogen to any carbon monoxide present of at least 5:1, and preferably hydrogen in the substantial absence of carbon monoxide.

The invention will be further described with respect to a process for the production of triptane as a desired branched chain hydrocarbon reaction product, it being understood that other branched chain hydrocarbons may be produced by the present invention.

In a continuous or semi-continuous process for the production of triptane, the methanol and/or dimethyl ether fed to the reactor may be introduced continuously or semi-continuously, preferably continuously.

In one embodiment, the second liquid phase, if present, is separated from the first liquid phase, and recovered from the reactor. The second liquid phase, if present, generally comprises the desired triptane product. The second liquid phase may also comprise triptene, which may be converted to the desired triptane product. Triptane is useful in the production of motor and aviation gasoline, especially, unleaded motor and unleaded aviation gasoline. The second phase will also comprises other hydrocarbon compounds, such as other branched chain hydrocarbons, some or all of which may also be useful in the production of motor and aviation gasoline. In addition, some of the other hydrocarbon compounds, especially by-product compounds, may be useful other than in the production of motor and aviation gasoline.

Typical useful compounds may include, for example, $C_4$ to $C_8$ branched chain alkanes (other than triptane) and $C_4$ to $C_8$ branched chain alkenes, such as iso-butene, iso-pentene and 2,3-dimethylbutene. Further useful compounds may include, for example, aromatic compounds, such as methyl-substituted benzene compounds, particularly tetramethylbenzenes and pentamethylbenzenes, which could, for example, be separated and subsequently used to produce xylenes, particularly p-xylene, which is useful as a feedstock for the manufacture of PTA.

Thus, the processes of the present invention may further comprise the step of recovering a second liquid phase from the reactor and recovering therefrom a triptane-containing hydrocarbon product. The recovered triptane-containing product may be employed as, or as an additive for, a motor or aviation gasoline, preferably, an unleaded motor or aviation gasoline. Preferably the second liquid phase may be purified, for example by distillation, to enhance its concentration of triptane. Optionally, at least one motor or aviation gasoline additive may be added to the hydrocarbons recovered from the recovered second liquid phase.

In the processes of the present invention, there will also be present in the reactor a vapour phase. The vapour phase may comprise at least one of hydrogen, water vapour, hydrocarbons (including triptane), methanol and/or dimethyl ether. In one embodiment, water is separated from the process by withdrawing at least some of the vapour phase from the reactor. The vapour may be condensed and purified, for example, by distillation, to enhance its concentration of triptane. The vapour phase may be purified by condensation and distillation to provide a product water stream clean enough for disposal, a hydrocarbon product comprising triptane and a recycle stream containing unreacted feed components.

In a preferred embodiment the processes of the present invention may be performed in an adiabatic reactor or a reactor with heat-removal cooling coils, which may remove up to 20% of the heat of reaction. In a preferred embodiment of a continuous process, the reactor is provided with a feed inlet through which in use passes co-joined recycle gases, fresh methanol and/or dimethyl ether and recycle methanol. In use, the methanol and/or dimethyl ether reacts, in the reactor, in the presence of a catalyst comprising indium halide to produce a mixture comprising water, hydrocarbons (including triptane) and unreacted methanol. Preferably, the reactor contains a hydrophilic liquid phase comprising the indium halide catalyst, a second, hydrophobic liquid phase comprising hydrocarbons, and a vapour phase comprising water and triptane. Water is removed from the reactor by removing vapour phase from the reactor. Triptane product may be recovered from the reactor from the vapour phase and/or from the liquid phase(s) removed from the reactor. Any catalyst components (halide and optionally indium) removed from the reactor in process streams removed for product recovery are recycled to the reactor to maintain in the reactor an effective concentration of catalyst comprising indium halide.

Methanol and or dimethyl ether present in the recovered vapour phase may be recycled to the reactor.

Suitable reactors and processes are further described, for example, in WO 02/070440, the contents of which are herein incorporated by reference.

Where the hydrocarbon reaction product comprising triptane is to be used as a blending component for a gasoline it is preferably distilled first to concentrate the triptane fraction, and any triptene fraction. Preferably, prior to use as a blending component for a gasoline the hydrocarbon reaction product is hydrogenated to convert any triptene and/or other alkenes to triptane and/or other alkanes.

There are a number of preferred ways in which the processes of the present invention may be used, some of which are described below.

(A) The process of the present invention may involve reacting methanol and/or dimethyl ether and the indium halide, to form a mixture of methanol and/or dimethyl ether and a hydrocarbon reaction product comprising triptane. The hydrocarbon reaction product may then be separated from the methanol and/or dimethyl ether, from the indium halide or both, for example, by separation as a different liquid phase or by distillation. The hydrocarbon reaction product may then be separately hydrogenated with hydrogen over a hydrogenation catalyst as described above, for example, at a pressure of 1-10 bar and a temperature of 10-100° C., preferably, 10-50° C. The hydrogenation converts any triptene (and other alkenes) to triptane (and other alkanes).

(B) Alternatively, instead of separating the hydrocarbon reaction product before hydrogenating the product, the hydrogenation can be performed prior to separation. After hydrogenation the triptane and other alkanes can be separated by distillation from the methanol or dimethyl ether, which can be recycled for reuse.

(C) In another alternative, the reaction of the methanol and/or dimethyl ether with the indium halide may be performed at least in part in the presence of hydrogen, either in the presence or absence of the hydrogenation catalyst. At the desired conversion point, the hydrocarbon reaction product can be separated from the indium halide, and optionally from the methanol and/or dimethyl ether, preferably followed by hydrogenation over the catalyst especially if no hydrogenation catalyst were used in the indium halide reaction step. If desired, the hydrogenation catalyst may be used in both steps. If the hydrocarbon reaction product contains no triptene, then the hydrocarbon reaction product is preferably separated from the indium halide, and optionally the methanol and/or dimethyl ether without any further hydrogenation.

In all these three alternatives (A) to (C), co-product water is separated in a vapour phase from indium halide catalyst which is retained in a liquid or solid phase.

The invention will now be illustrated with respect to the following examples:

Comparative Experiment A $ZnI_2$ (9.35 g), methanol (1.88 g) and ethanol (0.17 g) were weighed into a 15 ml ACE™ glass pressure tube. The contents were then agitated with a spatula and shaken to dissolve most of the $ZnI_2$. Some heat was evolved.

Once the tube and contents had cooled methyl iodide, 0.07 g, was added and the tube sealed. The tube was encased in steel mesh and placed in an oven at 200° C. for 2 hours.

On cooling the tube contained two liquid layers plus a large amount of off-white precipitate. The top organic layer was clear and an aliquot was removed for gas chromatographic (GC) analysis. This aliquot was diluted in $CDCl_3$ prior to GC analysis. The bottom liquid layer was dark brown/red in colour.

GC analysis showed the organic layer to contain a range of branched chain hydrocarbons, including iso-butane, iso-pentane, 2-methyl-2-butene, 2,3-dimethylbutane, triptane and triptene. In terms of hydrocarbons present (i.e. excluding methanol, $CDCl_3$, dimethyl ether and methyl iodide) the organic layer contained 20.1% by weight triptane, 1.1% by weight 2-methyl-2-butene, 2.8% by weight triptene and 4.9% by weight hexamethylbenzene.

EXAMPLE 1

The method of Comparative Experiment A was repeated except that an equivalent molar amount of $InI_3$ was used instead of $ZnI_2$.

$InI_3$ (14.38 g), methanol (1.87 g) and ethanol (0.17 g), were weighed into a 15 ml ACE™ glass pressure tube. The contents were then agitated with a spatula and shaken to dissolve the $InI_3$, all of which dissolved. Some heat was evolved.

Once the tube and contents had cooled methyl iodide, 0.08 g, was added and the tube sealed. The tube was encased in steel mesh and placed in an oven at 200° C. for 2 hours.

On cooling the tube contained two liquid layers and negligible precipitate.

The top organic layer was clear and an aliquot was removed for GC analysis. This aliquot was diluted in $CDCl_3$ prior to GC analysis.

GC analysis showed the organic layer to contain a range of branched chain hydrocarbons, including significant amounts of iso-butane, iso-pentane, 2,3-dimethylbutane and triptane.

In terms of the hydrocarbon product distribution, the branched chain hydrocarbon products produced in Example 1 were observed to be predominantly alkanes. By comparison, Comparative Experiment A showed significantly more alkene products. More specifically, in terms of hydrocarbons present (i.e. excluding methanol, $CDCl_3$, dimethyl ether and methyl iodide) the organic layer contained 26.4% by weight triptane and 0.4% by weight hexamethylbenzene. The organic layer contained negligible amounts of 2-methyl-2-butene and triptene.

Example 1 also showed increased iso-pentane and 2,3-dimethylbutane products compared to Comparative Experiment A (relative to both triptane and overall "heavies", where "heavies" are compounds having 8 or more carbon atoms, such as tetramethylbenzenes, pentamethylbenzene and hexamethylbenzene).

Although Example 1 did show increased pentamethylbenzene and tetramethylbenzenes compared to Comparative Experiment A, relative to the amount of triptane produced the overall "heavies" production was also lower.

Thus, Example 1 shows that use of indium iodide as a catalyst instead of zinc iodide leads to significant production of triptane, and without significant precipitation. Further the product distribution, when compared to Comparative Experiment A, is directed towards increased branched chain alkanes compared to branched chain olefins, and with reduced "heavies" production compared to "lights" production ("lights" generally being compounds having 6 or less carbon atoms).

EXAMPLE 2

The method of Example 1 was repeated, except that MTBE was used in the reaction in place of ethanol.

$InI_3$ (14.80 g), methanol (1.92 g) and MTBE (0.20 g), were weighed into a 15 ml ACET™ glass pressure tube. The contents were then agitated with a spatula and shaken to dissolve the $InI_3$, all of which dissolved. Some heat was evolved.

Once the tube and contents had cooled methyl iodide, 0.09 g, was added and the tube sealed. The tube was encased in steel mesh and placed in an oven at 200° C. for 2 hours.

On cooling the tube contained two liquid layers and negligible precipitate.

The top organic layer was clear and an aliquot was removed for GC analysis. This aliquot was diluted in $CDCl_3$ prior to GC analysis.

GC analysis showed the organic layer to contain a range of branched chain hydrocarbons, including significant amounts of iso-butane, iso-pentane, 2,3-dimethylbutane and triptane.

In terms of the hydrocarbon product distribution, the branched chain hydrocarbon products produced in Example 2 were observed to be predominantly alkanes. By comparison, Comparative Experiment A showed significantly more alkene products.

More specifically, in terms of hydrocarbons present (i.e. excluding methanol, $CDCl_3$, dimethyl ether and methyl iodide) the organic layer contained 25.3% by weight triptane and 0.1% by weight hexamethylbenzene. The organic layer contained negligible amounts of 2-methyl-2-butene and triptene.

Example 2 also showed increased iso-pentane and 2,3-dimethylbutane products (relative to both triptane and overall "heavies") compared to Comparative Experiment A.

Although Example 2 did show increased pentamethylbenzene and tetramethylbenzenes compared to Comparative Experiment A, relative to the amount of triptane produced the overall "heavies" production was also lower.

Thus, Example 2 shows that use of indium iodide as a catalyst instead of zinc iodide leads to significant production of triptane, and without significant precipitation. Further the product distribution, when compared to Comparative Experiment A, is directed towards increased branched chain alkanes compared to branched chain olefins, and with reduced "heavies" production compared to "lights" production.

Comparative Experiment B $ZnI_2$ (2.33 g), methanol (1.87 g) and ethanol (0.17 g), were weighed into a 15 ml ACE™ glass pressure tube. The contents were then agitated with a spatula and shaken to dissolve the $ZnI_2$, all of which dissolved. Some heat was evolved. Once the tube and contents had cooled methyl iodide (0.40 g) and 2-methyl-2-butene (0.005 g) were added and the tube sealed. The tube was encased in steel mesh and placed in an oven at 200° C. for 2 hours.

On cooling the tube contained only one liquid layer, which was red/brown in colour. There was no organic layer.

Hence, at this concentration, the zinc iodide catalyst has no, or only negligible, activity.

EXAMPLE 3

The method of Comparative Experiment B was repeated except that $InI_3$ was added to the reaction in addition to $ZnI_2$.

$InI_3$ (3.63 g), $ZnI_2$ (2.33 g), methanol (1.87 g) and ethanol (0.17 g), were weighed into a 15 ml ACET™ glass pressure tube. The contents were then agitated with a spatula and shaken to dissolve the $InI_3$ and $ZnI_2$, all of which dissolved. Some heat was evolved.

Once the tube and contents had cooled methyl iodide (0.40 g) and 2-methyl-2-butene (0.005 g) were added and the tube sealed. The tube was encased in steel mesh and placed in an oven at 200° C. for 2 hours.

On cooling the tube contained two liquid layers and a small amount of off-white precipitate. The top organic layer was clear and an aliquot was removed for GC analysis. This aliquot was diluted in $CDCl_3$ prior to GC analysis.

GC analysis showed the organic layer to contain a range of branched chain hydrocarbons, including iso-butane, 2-methyl-2-butene, iso-pentane, 2,3-dimethylbutane, triptane and triptene.

In terms of the hydrocarbon product distribution, the branched chain hydrocarbon products produced in Example 3 were observed to be predominantly alkanes.

More specifically, in terms of hydrocarbons present (i.e. excluding methanol, $CDCl_3$, dimethyl ether and methyl iodide) the organic layer contained 26.4% by weight triptane and 8.7% by weight hexamethylbenzene. The organic layer contained only small amounts of 2-methyl-2-butene (0.1% by weight) and negligible amounts of triptene. In addition, only small amounts of pentamethylbenzene and tetramethylbenzenes were present.

This example shows that a mixture of indium halide and zinc halide catalyst may be used.

Comparative Experiment C $ZnI_2$ (9.30 g) and methanol (2.01 g) were weighed into a 15 ml ACE™ glass pressure tube. The contents were then agitated with a spatula and shaken to dissolve the $ZnI_2$, most of which dissolved. Some heat was evolved. Once the tube and contents had cooled methyl iodide (0.40 g) and 2-methyl-2-butene (0.005 g) were added and the tube sealed. The tube was encased in steel mesh and placed in an oven at 200° C. for 2 hours. On cooling the tube contained two liquid layers and a large amount of an off-white precipitate. The lower layer was red/dark brown in colour. The tube was cooled in ice water and cyclohexane was added to the top organic layer as an internal standard, the contents of the tube shaken and then allowed to settle. An aliquot (50 µl) of the top organic layer was removed for gas chromatographic (GC) analysis. This aliquot was diluted in $CDCl_3$ (250 µl) prior to GC analysis.

GC analysis showed the organic layer to contain a range of branched chain hydrocarbons, including substantial amounts of triptane and triptene. The detailed product distribution of hydrocarbons present (i.e. excluding methanol, $CDCl_3$, dimethyl ether and methyl iodide) is given in Table 2.

EXAMPLE 4

The method of Comparative Experiment C was repeated except that $InI_3$ was used in the reaction in place of $ZnI_2$.

$InI_3$ (14.47 g) and methanol (2.00 g) were weighed into a 15 ml ACE™ glass pressure tube. The contents were then agitated with a spatula and shaken to dissolve the $InI_3$ most of which dissolved. Some heat was evolved.

Once the tube and contents had cooled methyl iodide (0.40 g) and 2-methyl-2-butene (0.005 g) were added and the tube sealed. The tube was encased in steel mesh and placed in an oven at 200° C. for 2 hours.

On cooling the tube contained two liquid layers and negligible precipitate. Some small colourles's crystals were also observed on the side of the tube above the liquid layers. The lower layer was red/dark brown in colour. The tube was cooled in ice water and cyclohexane was added to the top organic layer as an internal standard, the contents of the tube shaken and then allowed to settle. An aliquot (50%1) of the top organic layer was removed for gas chromatographic (GC) analysis. This aliquot was diluted in $CDCl_3$ (250 µl) prior to GC analysis.

GC analysis showed the organic layer to contain a range of branched chain hydrocarbons, including substantial amounts of triptane. The detailed product distribution of hydrocarbons present (i.e. excluding methanol, dimethyl ether, $CDCl_3$, cyclohexane and methyl iodide) is given in Table 2.

The total volume of the organic layer in Example 4 was observed to be approximately 50% less than that of Comparative Experiment C (also supported by the relative GC peak sizes of the cyclohexane internal standard).

In terms of the hydrocarbon product distribution, the branched chain hydrocarbon products produced in Example 4 were observed to be predominantly alkanes, whereas Comparative Experiment C produced significant quantities of triptene and 2-methyl-2-butene.

More specifically, the organic layer in Comparative Experiment C contained 18.87% by weight triptane, 3.79% by weight triptene, 56.21% by weight of "heavies" other than hexamethylbenzene, and 6.51% of hexamethylbenzene. In contrast, the organic layer in Example 4 contained 29.95% by weight triptane, only 27.77% by weight of "heavies" other than hexamethylbenzene, and 6.10% of hexamethylbenzene. Example 4 showed increased iso-pentane and 2,3-dimethylbutane products relative to both triptane and overall "heavies" compared to Comparative Experiment C.

Example 4 also showed increased pentamethylbenzene and tetramethylbenzenes compared to Comparative Experiment C, but the amount of triptane produced relative to the overall "heavies" production was significantly lower for Example 4.

Thus, Example 4 shows that use of indium iodide as a catalyst instead of zinc iodide leads to significant production of triptane, and without significant precipitation. Further the product distribution, when compared to Comparative Experiment C, is directed towards increased branched chain alkanes compared to branched chain olefins, and with reduced "heavies" production compared to "lights" production.

The charge compositions for the various experiments are summarised in Table 1.

TABLE 1

Charge compositions for methanol homologation reactions

| Experiment | Catalyst/g | Methanol/g | Alcohol or ether/g | Methyl iodide/g | Olefin/g |
|---|---|---|---|---|---|
| A | $ZnI_2$ 9.35 | 1.88 | Ethanol/0.17 | 0.07 | — |
| 1 | $InI_3$ 14.38 | 1.87 | Ethanol/0.17 | 0.08 | — |
| 2 | $InI_3$ 14.80 | 1.92 | MTBE/0.20 | 0.09 | — |
| B | $ZnI_2$ 2.33 | 1.87 | Ethanol/0.17 | 0.40 | 2-methyl-2-butene/0.005 g |
| 3 | $ZnI_2$ 2.33 $InI_3$ 3.63 | 1.87 | Ethanol/0.17 | 0.40 | 2-methyl-2-butene/0.005 g |
| C | $ZnI_2$ 9.30 | 2.01 | — | 0.40 | 2-methyl-2-butene/0.005 g |
| 4 | $InI_3$ 14.47 | 2.00 | — | 0.40 | 2-methyl-2-butene/0.005 g |

TABLE 2

Product Distribution for Comparative Experiment C and Example 4

| Compound | Comparative Experiment C Normalised % w/w** | Example 4 Normalised % w/w** |
|---|---|---|
| iso-butane | 3.33 | 4.93 |
| n-butane | 0.03 | 0.27 |
| iso-pentane | 3.31 | 12.27 |
| n-pentane | 0.01 | 0.25 |
| 2-methyl-2-butene | 1.06 | 0.00 |
| 2,3-dimethylbutane | 1.82 | 5.13 |
| 2-methylpentane | 0.52 | 3.48 |
| 3-methylpentane | 0.39 | 2.42 |
| Triptene | 3.79 | 0.00 |
| Triptane | 18.87 | 29.95 |
| Heavies* | 56.21 | 27.77 |
| HMB | 6.51 | 6.10 |
| Total | 95.85 | 92.56 |
| Balance (unknowns) | 4.15 | 7.44 |
| Ratio triptane to heavies including HMB | 0.30 | 0.88 |
| Ratio iso-pentane to heavies including HMB | 0.05 | 0.36 |
| Ratio 2,3-dimethylbutane to heavies including HMB | 0.03 | 0.15 |

*Excluding HMB.
**Normalised to hydrocarbons made (excludes $CDCl_3$, MeI, MeOH, DME and cyclohexane).

The invention claimed is:

1. A process for the production of branched chain hydrocarbons from methanol and/or dimethyl ether, which process comprises contacting, in a reactor, methanol and/or dimethyl ether with a catalyst comprising indium halide.

2. A process as claimed in claim 1, wherein the indium halide is one or more of InX and/or $InX_3$, wherein X is a halide selected from the group consisting of Cl, Br, I, and combinations thereof.

3. A process as claimed in claim 1, wherein, as well as the indium halide, the reactor also contains zinc halide.

4. A process as claimed in claim 1, wherein in addition to methanol and/or dimethyl ether reactants, there may also be introduced to the reactor additional feedstock components selected from the group consisting of hydrocarbons, halogenated hydrocarbons and oxygenated hydrocarbons.

5. A process as claimed in claim 4, wherein the additional feedstock components are selected from the group consisting of olefins, dienes, alcohols and ethers.

6. A process as claimed in claim 4, wherein the additional feedstock components act as initiators and/or promoters for the reaction to produce branched chain hydrocarbons.

7. A process as claimed in claim 6, wherein the reactor contains one or more compounds that act as initiators for the reaction selected from the group consisting of alcohols, ethers, olefins and dienes having at least 2 carbon atoms.

8. A process as claimed in claim 6, wherein there is present in the reactor one or more promoters selected from the group consisting of one or more of hydrogen halides and alkyl halides of 1 to 8 carbon atoms.

9. A process as claimed in claim 1, wherein the process is operated in the liquid phase.

10. A process as claimed in claim 1, wherein the methanol and/or dimethyl ether is contacted with the indium halide at a temperature of 100 to 300° C.

11. A process as claimed in claim 1, wherein the reaction is performed at a pressure in the range 1-100 barg.

12. A process as claimed in claim 1, wherein the reaction is performed in the presence of hydrogen.

13. A process as claimed in claim 1, wherein the reaction is performed in the presence of a hydrogenation catalyst.

14. A process as claimed in claim 1, wherein the reaction is performed in the presence of carbon monoxide.

15. A process as claimed in claim 1, which process is a continuous or semi-continuous process for the production of branched chain hydrocarbons from methanol and/or dimethyl ether which process comprises contacting, in a liquid phase reaction composition in a reactor, methanol and/or dimethyl ether with a catalyst comprising indium halide, and at a temperature of at least 100° C., to produce a product mixture comprising (i) methanol and/or dimethyl ether and (ii) branched chain hydrocarbons, and in which process the catalyst is maintained in the reactor in an active form and in an effective concentration.

16. A process as claimed in claim 15, wherein the catalyst comprising indium halide is maintained in an active form and in an effective concentration in the reactor by recycling to the reactor, one or more promoter compounds from downstream product recovery stage(s).

17. A process as claimed in claim 16, wherein the liquid reaction composition also comprises at least one further additional feedstock component.

18. A process as claimed in claim 17, wherein said further additional feedstock component has been recycled from downstream product recovery stage(s).

* * * * *

UNITED STATES PATENT AND TRADEMARK OFFICE
CERTIFICATE OF CORRECTION

PATENT NO. : 7,642,392 B2
APPLICATION NO. : 10/569441
DATED : January 5, 2010
INVENTOR(S) : Kay et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this

Twenty-first Day of December, 2010

David J. Kappos
*Director of the United States Patent and Trademark Office*